US00PP35146P2

(12) United States Plant Patent
Verhoef

(10) Patent No.: US PP35,146 P2
(45) Date of Patent: May 2, 2023

(54) ***WEIGELA* PLANT NAMED 'VERWEIG9'**

(50) Latin Name: *Weigela florida*
Varietal Denomination: VERWEIG9

(71) Applicant: Gijsbertus Verhoef, Hazerswoude (NL)

(72) Inventor: Gijsbertus Verhoef, Hazerswoude (NL)

(73) Assignee: Spring Meadow Nursery, Grand Haven, MI (US)

( * ) Notice: Subject to any disclaimer, the term of this patent is extended or adjusted under 35 U.S.C. 154(b) by 106 days.

(21) Appl. No.: 17/839,845

(22) Filed: Jun. 14, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Weigela* plant named 'VERWEIG9' is disclosed, characterized by dynamic foliage color, changing from green with a bonze tint in the Spring to orange-bronze in the Summer, and bright red in the Fall. Plants are compact and globose in habit. Flowers are bright pink. The new variety is a *Weigela*, normally produced as an outdoor garden plant.

4 Drawing Sheets

Latin name of the genus and species: *Weigela florida*.
Variety denomination: 'VERWEIG9'.

BACKGROUND OF THE INVENTION

The new *Weigela* cultivar is a product of open pollination conducted by the inventor in Hazerswoude, the Netherlands. The objective of the breeding program was to produce new *Weigela* plants with novel foliage colors and dwarf plant habits. The crossing resulting in this new variety was made during the Summer 2013.

The seed parent is the variety *Weigela florida* 'Verwof 1', U.S. Plant Pat. No. 30,866. The pollen parent is the unpatented proprietary *Weigela florida* variety referred to as '*Weigela* bv005'. The new variety was identified as a potentially interesting selection in Summer 2015, at a nursery in Hazerswoude, the Netherlands.

Asexual reproduction of the new cultivar 'VERWEIG9' by softwood cuttings was first performed in the Summer of 2015, at a nursery in Hazerswoude, the Netherlands. Subsequent propagation has shown that the unique features of this cultivar are stable and reproduced true to type in multiple successive generations.

SUMMARY OF THE INVENTION

The cultivar 'VERWEIG9' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VERWEIG9'. These characteristics in combination distinguish 'VERWEIG9' as a new and distinct *Weigela* cultivar;

1. Dynamic foliage color, changing from green with a bonze tint in the Spring to orange-bronze in the Summer, and bright red in the Fall.

2. Compact growth habit.
3. Globose plant form.
4. Bright pink flowers.

PARENT COMPARISON

Plants of the new cultivar 'VERWEIG9' are similar to plants of the seed parent in most horticultural characteristics, however, plants of the new cultivar 'VERWEIG9' differ in the following;

1. Foliage of the new cultivar turns bright red in the Fall; foliage of the seed parent develops only red leaf margins in the Fall.
2. Foliage of the new variety turns bronze-orange in Summer; foliage of the seed parent transitions directly from lime green to green with brown-red margins.

Plants of the new cultivar 'VERWEIG9' are similar to plants of the pollen parent in most horticultural characteristics, however, plants of the new cultivar 'VERWEIG9' differ in the following;

1. Foliage of the new cultivar is not variegated; foliage of the pollen parent is variegated.
2. Mature plants of the new variety are shorter than mature plants of the pollen parent.

COMMERCIAL COMPARISON

Plants of the new cultivar 'VERWEIG9' can be compared to the commercial variety *Weigela* 'Wings of Fire', U.S. Plant Pat. No. 21,920. These varieties are similar in most horticultural characteristics, however 'VERWEIG9' differs in the following;

1. New cultivar has leaves with a most flat aspect; foliage of this comparator is strongly concave.
2. Foliage of the new variety transitions from dark green to bronze to bright red; foliage of this comparator transitions from lime green to dark red.

BRIEF DESCRIPTION OF THE PHOTOGRAPHS

The accompanying photograph in FIG. 1 illustrates in full color typical Spring foliage color of 'VERWEIG9' during Spring.

Figure 1:
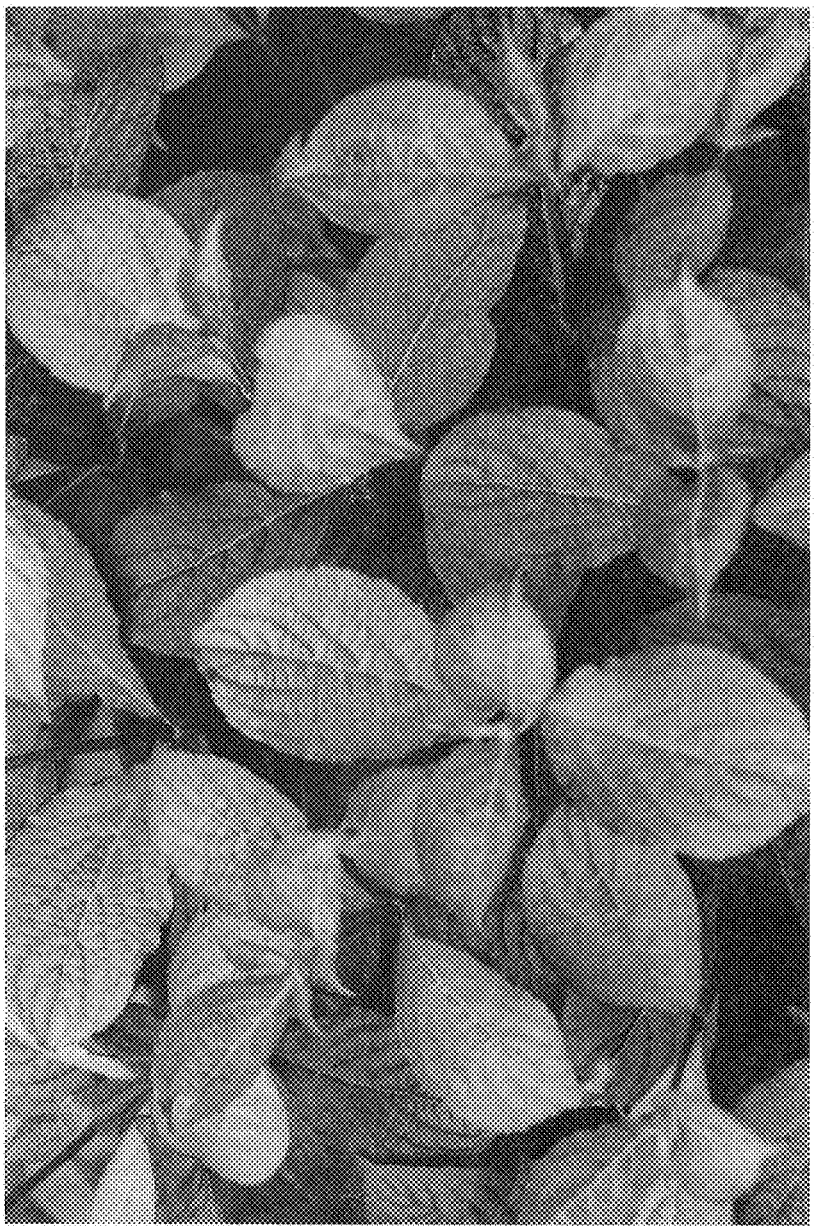
Figure 2:
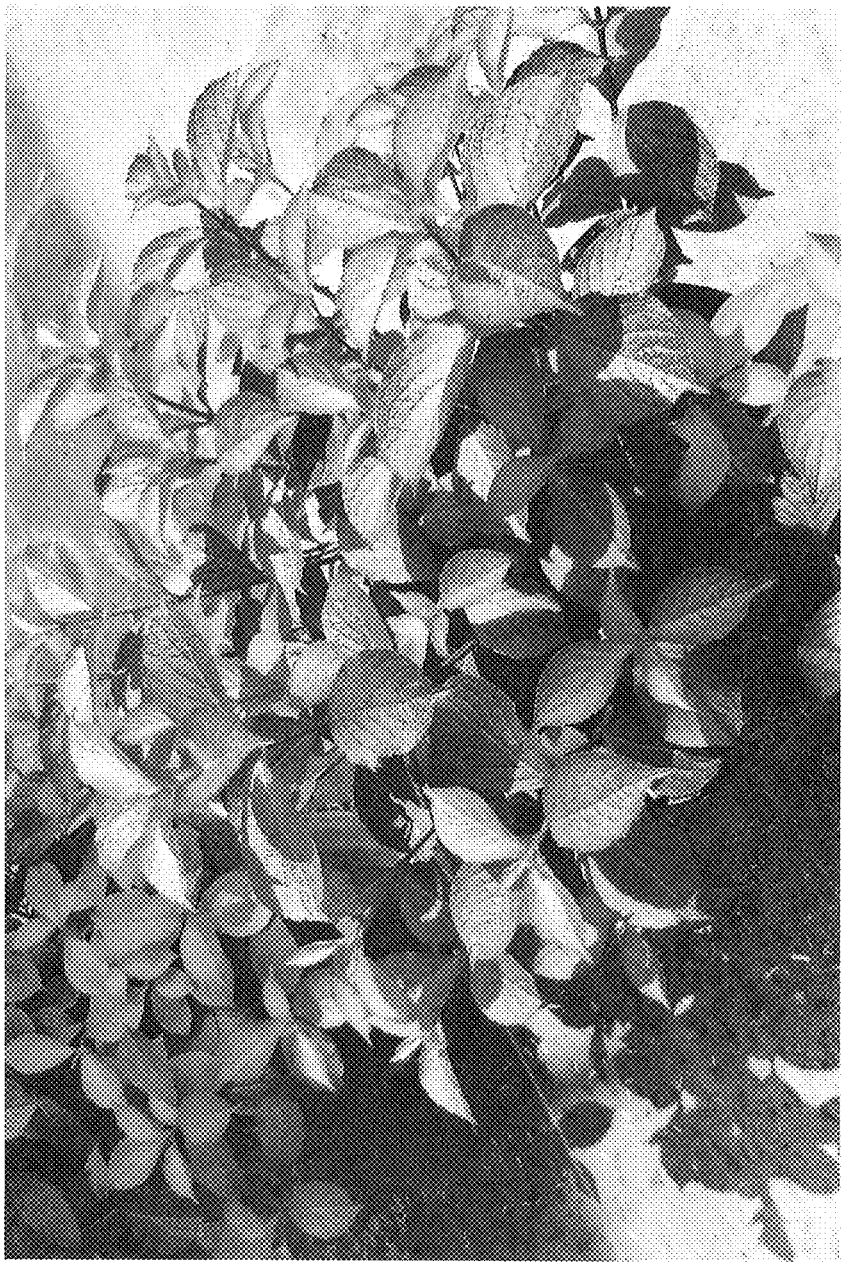
FIG. 2 illustrates typical plants grown in a 2-gallon pot, at about 1.5 years of age, in the Summer with typical Summer foliage coloration.
Figure 3:
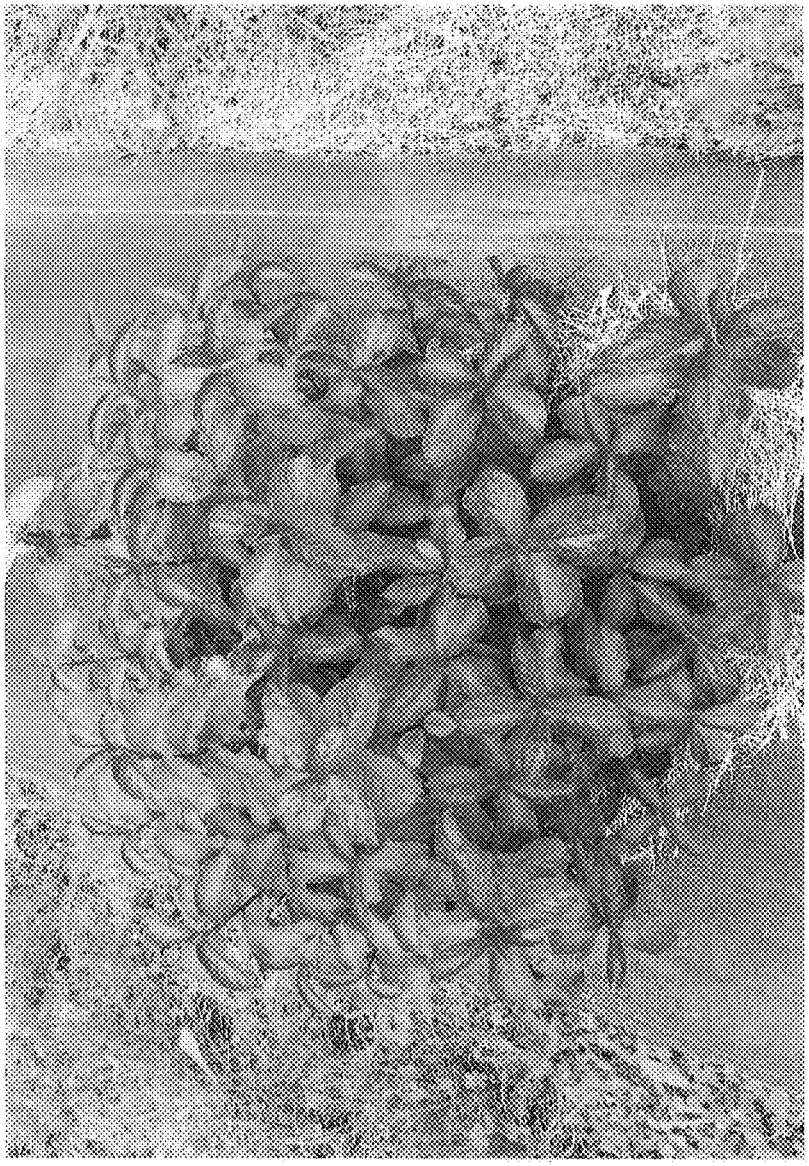
FIG. 3 illustrates in full color typical plants of 'VERWEIG9' with typical fall foliage color in a ground bed at about 2 years of age.
Figure 4:
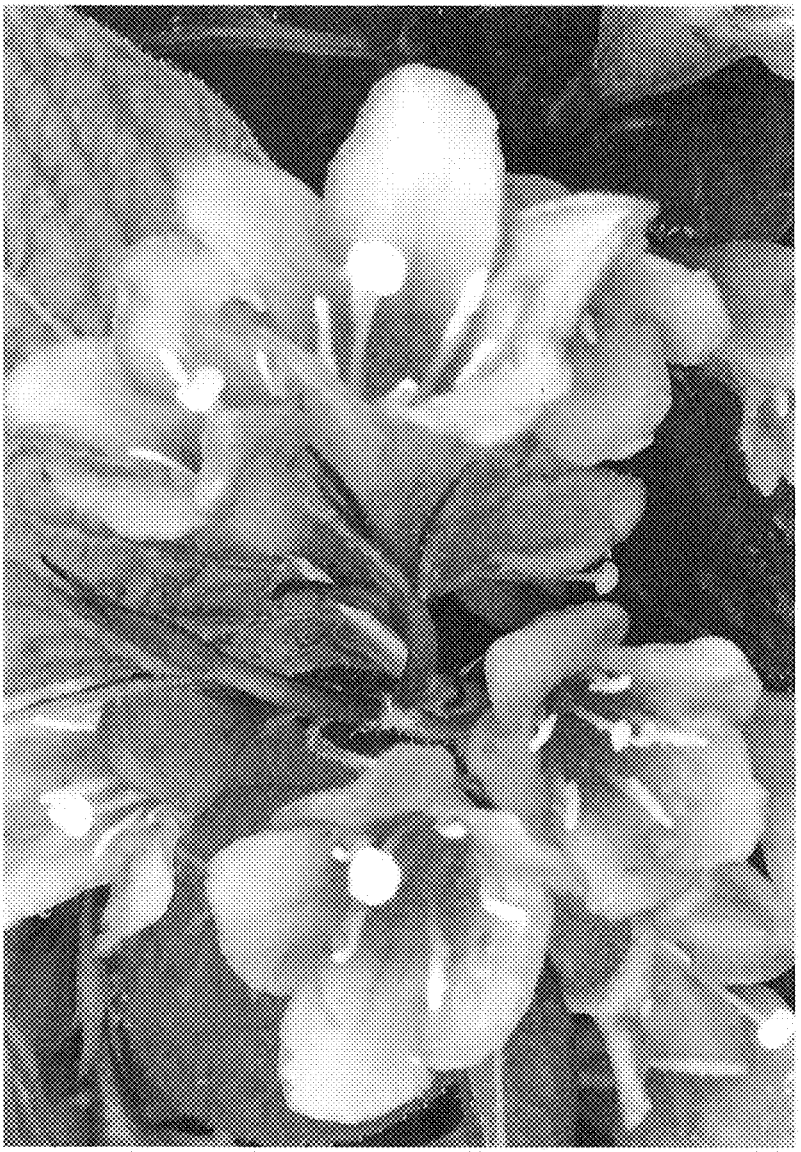
FIG. 4 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'VERWEIG9' plants grown in a polyhouse in Grand Haven, Mich. Measurements were taken during May of 2021. The plants were 2 to 3 years old. The growing temperature ranged from approximately 18° C. to 27° C. during the day and 5° C. to 10° C. at night. Measurements and numerical values represent averages of typical plant types.

Botanical classification: *Weigela florida* 'VERWEIG9'.

PROPAGATION

Time to initiate roots: Approximately 15 days at 18° C. to 27° C.

Root description: Density is dense and freely branching. Thin and fibrous. White in color, not effectively measured with a color chart.

Time to produce a rooted young plant: Approximately 60 days.

PLANT

Plant type: Perennial shrub.
Age of plant described: Approximately 2 to 3 years old.
Growth habit: Compact.
Pot size of plant described: 3-gallon container.
Overall plant shape: Globose.
Height: 40 cm unpruned in a 3-gallon pot.
Plant spread: 40 cm unpruned in a 3-gallon pot.
Plant vigor: Vigorous although compact.
Branching characteristics: Basal, very free branching.
Length of primary lateral branches: 30 cm.
Diameter of lateral branches: 4 mm.
Quantity of lateral branches: About 25.
Stem:
- *Stem characteristics*.—Rounded, two small ridges 180° apart on stem.
- *Stem strength*.—Strong and somewhat flexible.
- *Aspect*.—45° to 90°.
- *Color*.—New Growth near RHS Greyed-Orange 166B. Mature Growth: Near RHS Grey-Brown 199C.
- *Pubescence*.—slight pubescence on ridges.

Internode length: Average 3 to 5 cm.

FOLIAGE

Leaf:
- *Arrangement*.—Opposite.
- *Leaf shape*.—Elliptic to oblanceolate.
- *Average length*.—Approximately 6 cm.
- *Average width*.—4 cm.
- *Apex*.—Acuminate.
- *Base*.—Oblique.
- *Margin*.—Serrulate.
- *Texture of top surface*.—Rough, coriaceous.
- *Texture of bottom surface*.—Rough, coriaceous with ridged veins.
- *Pubescence*.—On underside midrib.
- *Color*.—Spring Young foliage upper side: Near RHS Yellow-green 146A with tinges of Greyed-orange 177A and Greyed-orange 176B. Some foliage flushed Brown 200A and 200B. Spring Young foliage under side: Near RHS Yellow-green 146B with tinges of Greyed-orange 177A and Greyed-orange 176B. Summer Mature foliage upper side: Near RHS Greyed-orange 177A and Greyed-orange 176B. Summer Mature foliage under side: Near RHS Greyed-orange 177A and Greyed-orange 176B. Fall foliage upper side: Near RHS Greyed-Red 183A. Fall foliage under side: Near RHS Greyed-Purple 185B.
- *Venation*.—Pattern: Pinnate. Color upper side: Near RHS Yellow-green 146B with variable tinges of Greyed-orange 174B. Color under side: Near RHS Yellow-green 146B with variable tinges of Greyed-orange 174B.
- *Petiole*.—Length: 3 mm. Diameter: 2 mm. Petiole color upper side: Near RHS Yellow-green 146B with variable tinges of Greyed-orange 174B. Petiole color lower side: Near RHS Yellow-green 146B with variable tinges of Greyed-orange 174B. Petiole Texture: Some pubescence.
- *Other foliage characteristics*.—Good durability to environmental stressors.

FLOWER

Natural flowering season: Late Spring to early Summer.
Inflorescence type and habit: Umbel.
Inflorescence height: 6 cm.
Inflorescence width: 8 cm.
Quantity of flowers per inflorescence: 3 to 7.
Quantity of flowers and buds per lateral stem: About 50.
Individual flowers:
- *Flower shape*.—Salverform.
- *Flower aspect*.—Upright and outward facing.
- *Flowering arrangement*.—Single salverform flower, majority grouped in 6-10.
- *Size*.—Diameter: 2.0 cm to 2.5 cm. Depth: 3 cm. Throat diameter proximal: 1 cm. Throat diameter distal: 2 mm. Tube length: 1 cm.
- *Persistence*.—Self-cleaning.
- *Fragrance*.—Moderate, sweet.

Bud:
- *Shape*.—Obovate to spatulate.
- *Length*.—2.5 cm.
- *Diameter*.—10 mm.
- *Color*.—RHS Red-Purple 68B with 68A on throat.

Petal:

*Petal arrangement*.—Whorled, fused at opening of throat.

*Number of petals per flower*.—5.

*Petal shape*.—Rounded-orbicular.

*Petal base*.—Fused at throat.

*Margin*.—Entire, slightly undulate.

*Tip shape*.—Obtuse.

*Length*.—10 mm.

*Width*.—10 mm.

*Texture*.—Upper: Soft, smooth, delicate. Lower: Soft, smooth, delicate.

*Color*.—When opening: Upper side: RHS Red-Purple 68B. Under side: RHS Red-Purple 68B. Fully open: Upper side: RHS Red-Purple 68B. Under side: Mix of RHS Red-Purple 68B.

*Flower tube*.—Color: RHS Red-Purple 68A.

*Throat*.—Color: RHS Red-Purple 68B.

Sepal:

*Arrangement*.—Whorled, fused at base.

*Number*.—5.

*Shape*.—Narrowly triangular.

*Tip*.—Acuminate.

*Base*.—Obtuse.

*Margin*.—Entire.

*Length*.—6 mm.

*Width*.—1 mm.

*Texture, upper*.—Smooth, conaceous.

*Texture, lower*.—Smooth, conaceous.

*Color*.—Upper surface at maturity: RHS Yellow-green 146D with variable tinges of Greyed-orange 173A. Under surface at maturity: RHS Yellow-green 146D with variable tinges of Greyed-orange 173A.

Peduncle:

*Length*.—1 cm.

*Diameter*.—3 mm.

*Color*.—RHS Yellow-green 146D with variable tinges of Greyed-orange 173A.

*Orientation*.—Upright and outward.

*Strength*.—Strong.

*Texture*.—Lightly pubescent.

Pedicel: None.

REPRODUCTIVE ORGANS

Stamens:

*Number*.—5.

*Filament length*.—1 cm.

*Filament color*.—RHS White N155B, changing to Red-Purple 68B at base.

Anthers:

*Shape*.—Linear, slightly oblong.

*Length*.—4 mm.

*Color*.—RHS Greyed-Yellow 161C.

*Pollen color*.—RHS Greyed-Yellow 161C.

*Pollen amount*.—Moderate.

Pistil:

*Number*.—1.

*Length*.—3 cm.

*Style*.—Length: 2.7 cm. Color: RHS White N155B, changing to Red-Purple 68B at base. Ovary Color: RHS Red-Purple 68B.

Stigma:

*Color*.—RHS White N155B.

*Shape*.—Globular.

OTHER CHARACTERISTICS

Seeds and fruits: Not observed to set fruit and seeds.

Disease/pest resistance: Neither resistance nor susceptibility to normal diseases and pests of *Weigela* have been observed Temperature tolerance: The new variety tolerates temperatures between −31° C. to 38° C.

Environmental stressors: Good tolerance to wind and rain.

What is claimed is:

1. A new and distinct cultivar of *Weigela florida* plant named ‘VERWEIG9’ as herein illustrated and described.

* * * * *